(12) United States Patent
Park et al.

(10) Patent No.: US 7,435,411 B2
(45) Date of Patent: Oct. 14, 2008

(54) PAECILOMYCES GENUS MICROORGANISM AND MICROBIAL INSECTICIDE FOR CONTROLLING THE SOIL PESTS CONTAINING THE SAME

(75) Inventors: Ho Yong Park, Taejeon (KR); Kwang Hee Son, Taejeon (KR); Eun Young Suh, Kangwon-do (KR); Ki-Duk Kim, Taejeon (KR); Dong Ha Shin, Taejeon (KR)

(73) Assignee: Korea Research Institute of Bioscience and Biotechnology (KR)

( * ) Notice: Subject to any disclaimer, the term of this patent is extended or adjusted under 35 U.S.C. 154(b) by 50 days.

(21) Appl. No.: 10/494,110

(22) PCT Filed: Nov. 2, 2002

(86) PCT No.: PCT/KR02/02040

§ 371 (c)(1),
(2), (4) Date: Sep. 7, 2004

(87) PCT Pub. No.: WO03/038066

PCT Pub. Date: May 8, 2003

(65) Prior Publication Data

US 2005/0008619 A1 Jan. 13, 2005

(30) Foreign Application Priority Data

Nov. 2, 2001 (KR) ................................ 2001-68127

(51) Int. Cl.
*A01N 63/00* (2006.01)
*C12N 1/00* (2006.01)

(52) U.S. Cl. ................ 424/93.5; 424/195.15; 435/254.1

(58) Field of Classification Search ...................... None
See application file for complete search history.

(56) References Cited

U.S. PATENT DOCUMENTS

| | | | | |
|---|---|---|---|---|
| 4,985,364 A | * | 1/1991 | Hildebrand et al. | 435/136 |
| 5,360,607 A | * | 11/1994 | Eyal et al. | 424/93.5 |
| 5,750,126 A | * | 5/1998 | Smith et al. | 424/405 |
| 2002/0146394 A1 | * | 10/2002 | Stamets | 424/93.5 |

FOREIGN PATENT DOCUMENTS

| | | |
|---|---|---|
| JP | 11-012280 | 1/1999 |
| JP | 2000-083471 | 3/2000 |
| JP | 2001-078751 | 3/2001 |

* cited by examiner

*Primary Examiner*—L Blaine Lankford
*Assistant Examiner*—Taeyoon Kim
(74) *Attorney, Agent, or Firm*—Klarquist Sparkman, LLP

(57) ABSTRACT

The present invention relates to a *paecilomyces* genus microorganism and microbial insecticide for controlling the soil pests using the same, more particularly to a *paecilomyces* genus microorganism having insecticidal activity to soil pests and a microbial insecticide for controlling the soil pests containing the same. Since the microbial insecticide of the present invention shows excellent insecticidal activity to harmful soil pests, it can effectively be used as a environment-compatible insecticide to prevent the soil pests from farmland crops.

13 Claims, 5 Drawing Sheets

A

B

PAECILOMYCES GENUS MICROORGANISM AND MICROBIAL INSECTICIDE FOR CONTROLLING THE SOIL PESTS CONTAINING THE SAME

This is the U.S. National Stage of International Application No. PCT/KR02/02040, filed Nov. 2. 2002 (published in English under PCT Article 21(2)). which in turn claims the benefit of Korean patent application no. 2001/68127. filed Nov. 2. 2001.

FIELD OF THE INVENTION

The present invention relates to a novel *paecilomyces* genus microorganism and a microbial insecticide for controlling the soil pests using the same, more particularly to a *paecilomyces* genus microorganism having insecticidal activity to soil pests, a medium for mass-production of the microorganism and a microbial insecticide for controlling the soil pests containing the same.

BACKGROUND ART OF THE INVENTION

Insects have excellent ability to adapt to environment and have the widest species on earth (Wilson, O. and F. N. Peter., *Biodiversity.*, 1989, Washington, D.C. Natl. Acad. Press). Some of those insects harm to various major crops. Chemical insecticides have been used to control such pests. But such chemical insecticides have killed not only pests but also useful insects and parasites living in pests because of their wide spectrum. In addition, target pests cannot be controlled anymore by having resistance against chemical insecticides owing to the repeated exposure on them. Further, chemical insecticides are harmful for human body.

Various plants, trees and grasses are growing widely in golf courses, so that the appearance of pests is unique and the number of pests adapting to such ecosystem is increasing year after year. As a kind of soil pests, *Mimela splendems* (gold bug) is a euryphagous pest harming plants (42 families, 186 species), especially plants of *Rossaceae, Salicaceae, Fagaceae, Betulaceae* and *Aceraceae*. Some adults of gold bugs harm leaves of crops and plants and larvae do roots of various crops and grasses, making them major target pest of golf clubs. Indirectly, adults of the gold bugs steal onto greens and away with discharges during the night, causing interruption of a course of a golf ball. (Lee et al, Korean Journal of Applied Entomology, 1997, 36, 2, 156-165; Lee, PhD Thesis, 2000). Particularly, the larvae of soil pests including gold bugs harming major crops and grasses are troublesome since they damage the roots of plants and grasses. The larvae of gold bugs developing and living in golf courses directly harm grass roots to death and indirectly provide themselves as feed for birds, causing digging up the grass. Therefore, they have a bad effect on the preservation of grass quality.

To control such soil insects like gold bugs, fenitrothion emulsion, chlorpyrifos-methyl emulsion and ethoprophos granules have been used. But those chemical pesticides have effects on only just-hatched larvae (the first larva stage). Thus, catching the right time is essential for controlling those insects. By the way, those chemical pesticides weaken the grass and cause overdose (Korea Patent Application #1999-15472).

Great efforts have been made to control the soil pests like gold bugs, *Encarcia formosa, Eretmocerus eremicus, Plutella xylostella, Spodoptera litura* and *Nilaparvata lugens*. But using the conventional chemical pesticides causes not only high expense but also such problems that the destruction of ecosystem, the under water contamination, the residual toxicity in agricultural products and the appearance of insects having resistance. Thus, it is urgently required to develop an environment-friendly controlling method for controlling soil pests in order to minimize such problems.

As one way of environment-friendly controlling methods for pests, insect pathogenic microorganisms are now being used, which is characterized by working selectively for target pests only without harming human, animals and plants.

For the development of a microorganism for controlling soil pests, it is very important to determine the components and factors of medium for mass-production. Again, it is essential to prepare inexpensive and available medium in order to supply microbial insecticides that are less expensive than conventional chemical insecticides. Though, it is still hard to prepare such medium for mass-production since the growth speed and time of a target microorganism as well as biological, chemical and physical factors for the production ought to be considered together.

Thus, the present inventors have searched insect pathogenic microorganisms for controlling soil pests harming major crops and finally accomplished this invention by confirming the fact that a fungus of *Paecilomyces* genus killed soil pests including the larvae of gold bugs.

SUMMARY OF THE INVENTION

The present invention relates to a *paecilomyces* genus microorganism and microbial insecticide for controlling the soil pests using the same, more particularly to a *paecilomyces* genus microorganism having insecticidal activity to soil pests, a medium for mass-production of the microorganism and a microbial insecticide for controlling the soil pests containing the same. Since the microbial insecticide of the present invention shows excellent insecticidal activity to harmful soil pests, it can effectively be used as an environment-compatible insecticide to prevent the soil pests from farmland crops.

DETAILED DESCRIPTION OF THE INVENTION

Figure 1:
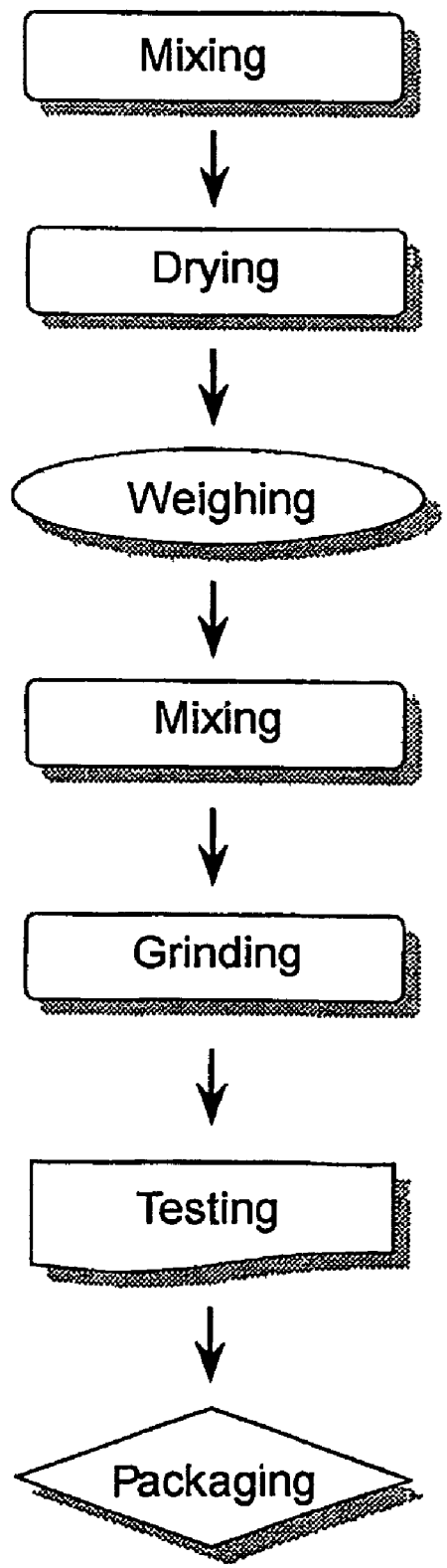
FIG. 1 is a diagram showing the manufacturing process of microbial insecticide wettable powders comprising the *Paecilomyces lilacinus* HY-4 of the present invention for controlling soil pests.

The present invention provides a novel fungus of *Paecilomyces* genus that is useful for controlling soil pests.

The present invention also provides a medium for mass-production of a fungus of *Paecilomyces* genus.

The present invention further provides a microbial insecticide comprising the above fungus of *Paecilomyces* genus for controlling soil pests and a preparation method thereof.

Further features of the present invention will appear hereinafter.

The present invention provides a *Paecilomyces* genus microorganism having insectisidal activity to soil pests.

The present inventors separated a microorganism having insecticidal effect on soil pests from dead insects infected with insect pathogenic microorganisms and soil samples where soil pests were inhabited. The microorganism of the present invention was identified as a kind of *Paecilomyces lilacinus*. The microorganism of the present invention was named as "*Paecilomyces lilacinus* HY-4" and deposited at Gene Bank of Korea Research Institute of Biosciene and Biotehnology on Oct. 27, 1997 (Accession No: KCTC 0395BP)

The present inventors investigated the insecticidal effect of the *Paecilomyces* genus microorganism of the present invention with the dipping method. As a result, the microorganism killed more than 50% larvae from the $1^{st}$ instar through the $3^{rd}$ instar and more larvae were proved to be infected with the *Paecilomyces* genus microorganism of the present invention as time went, suggesting the microorganism had excellent insecticidal effect on soil pests (see FIG. 3 and FIG. 4).

The present invention also provides a medium for mass-production of the above *Paecilomyces* genus microorganism.

In order to mass-produce the *Paecilomyces* genus microorganism economically, the present invention provides a standard medium prepared by mixing wheat bran and water. The above medium can contain one or more components selected from a group consisting of rice bran, glucose, yeast extract, cottonseed, $KNO_3$, phosphate and zeolite.

The major factor influencing largely on the culture of microorganism, especially in the case of solid culture, is moisture content, that is, the productivity of bacteria increases, the consuming speed of medium becomes faster and the number of produced live bacteria also increase as moisture content is high. Among the above additives, rice bran is used as a supplementary material for the increase of ventilation and the improvement of property of solid medium, glucose as an early growth factor, yeast extract as a source of nitrogen and microelements, cottonseed as a nitrogen source, $KNO_3$ as an inorganic nitrogen source, phosphate as a buffer for pH and zeolite is used as an absorbing inorganic additive having sustained releasing property of metallic elements and phosphate.

The present invention further provides a microbial insecticide comprising a *Paecilomyces* genus microorganism for controlling soil pests and a preparation method thereof.

Microbial insecticides of the present invention containing a *Paecilomyces* genus microorganism for controlling soil pests can be prepared in the form of either wettable powders, granules or capsules.

The wettable powders of the above microbial insecticides can be obtained by pulverization after drying solid media inoculated with *Paecilomyces* genus microorganism and mixing surfactant and diluents/nutrients with it.

Surfactants used for preparing wettable powders of the above microbial insecticides can be selected from a group consisting of polycarboxylate (Hannong chemicals Inc.), sodium lingosulfonate, calcium lignosulfonate, sodium dialkyl sulfosuccinate, sodium alkyl sulfonate, polyoxy ethylene alkyl phenyl ether, sodium tripolyphosphate (Hannong chemicals Inc.), sodium alkyl aryl sulfonate, polyoxyethylene alkyl phenyl ether, polyoxyethylene aryl phosphoric ester, polyoxyethylene alkyl aryl ether, polyoxyethylene alkyl aryl polymer, polyoxyethylene alkyl aryl polymer special, polyoxyalkylone alkyl phenyl ether, polyoxyethylene nonyl phenyl ether, sodium sulfonate naphthalene formaldehyde, triton 100 and tween 80. Diluents/nutrients can be selected from a group consisting of soybean flour, rice, wheat, yellow earth, diatomaceous earth, dextrin, glucose and starch.

For the preparation of the microbial insecticide granules for controlling soil pests containing the *Paecilomyces* genus microorganism, dried solid medium inoculated with the *Paecilomyces* genus microorganism, crushed thereof, and then added surfactants, diluents/nutrients and disintegrators.

The microbial insecticide granules of the present invention are preferably prepared with the following weight ratios: *Paecilomyces* genus microorganism spores 30-83 weight parts, surfactants 2-30 weight parts, diluents 5-20 weight parts, disintegrators 10-40 weight parts.

One or more surfactants can be selected from a group consisting of poly carboxylate, sodium lingosulfonate, calcium lignosulfonate, sodium dialkyl sulfosuccinate, sodium alkyl sulfonate, polyoxyethylene alkyl phenyl ether, sodium tripolyphosphate, sodium alkyl aryl sulfonate, polyoxyethylene alkyl phenyl ether, polyoxyethylene alkyl aryl phosphoric ester, polyoxyethylene alkyl aryl ether, polyoxyethylene alkyl aryl polymer, polyoxyethylene alkyl aryl polymer special, polyoxyalkylone alkyl phenyl ether, polyoxyethylene nonyl phenyl ether, sodium sulfonate naphthalene formaldehyde, triton 100 and tween 80, and used for the preparation of the above microbial insecticide granules. One or more diluents/nutrients can be selected from a group consisting of soybean flours, rice, wheat, diatomaceous earth, dextrin, glucose and starch. One or more disintegrators can be selected from a group consisting of bentonite, talc, dialite, kaoline and calcium carbonate.

In addition, the microbial insecticide granules of the present invention can additionally include one or more additives selected from a group consisting of surface active agents, inactive carriers, preservatives, wetting agents, supply accelerants, attractants, encapsulating agents, binders, emulsifiers, dyes, UV protectors, buffers and fluids.

The preparation method for microbial insecticide wettable powders of the present invention comprises the following steps:

1) Pulverizing after drying solid media inoculated with *Paecilomyces lilacinus* HY-4; and
2) Adding surfactants and diluents to the pulverized powders of the above step 1) and then pulverizing thereof again (see FIG. 1).

Figure 2:
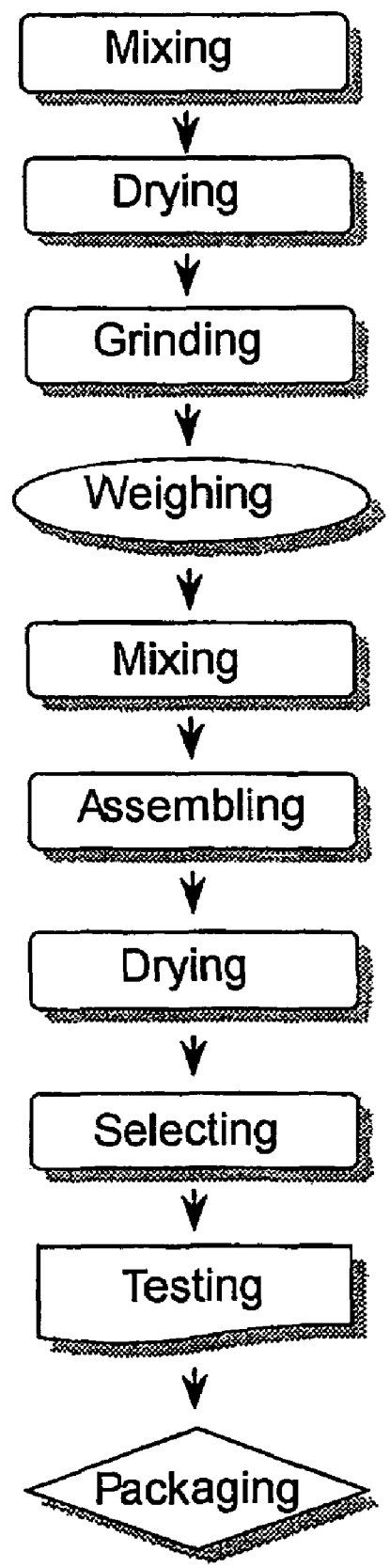
FIG. 2 is a diagram showing the manufacturing process of microbial insecticide granules comprising the *Paecilomyces lilacinus* HY-4 of the present invention for controlling soil pests.

And, the preparation method for microbial insecticide granules of the present invention comprises the following steps:

1) Pulverizing after drying solid media inoculated with *Paecilomyces lilacinus* HY-4;
2) Adding surfactants, adjuvant and diluents to the pulverized powders of the above step 1) and then kneading thereof with water; and
3) Granulating the dough prepared in the above step 2) and then drying thereof (see FIG. 2).

The present inventors investigated the insecticidal effect of the microbial insecticides for controlling soil pests containing the *Paecilomyces* genus microorganism on the larvae of gold bugs. As a result, the microbial insecticides of the present invention could kill more than 50% of the larvae and the chance for the larvae to be infected with the *Paecilomyces* genus microorganism went higher as time passed (see FIG. 3-FIG. 5).

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Separation and Identification of Microorganisms

In order to separate microorganisms that are useful for controlling soil pests, the present inventors collected dead insects infected with insect pathogenic microorganisms and at the same time, picked insects from soil samples where soil pests are inhibiting as well. Particularly, the present inventors crushed soil pests dead by infection with insect pathogenic microorganisms and diluted with sterile water. Took 0.1 ml of suspension and smeared on microorganism test medium (Dermatophyte test medium; DTM medium) as presented in Table 1. Suspended 0.1 g of soil samples with 5 ml of sterile water and smeared on microorganism test medium as well. Culture thereof at 30° C. for 5 days and made a selection, which was inoculated on new DTM medium and further cultured under the same condition above.

TABLE 1

| Ingredient | Amount (%) |
|---|---|
| Glucose | 2 |
| Soytone | 1 |
| Phenol Red | 0.02 |
| Cycloheximide | 0.05 |
| Chloheximide | 0.01 |
| Gentamycine | 0.01 |
| Agar | 1.5 |
| Acetone (w/w) | 2 |

As a result, the present inventors separated a microorganism showed excellent insecticidal effect on soil pests, and identified thereof as a kind of *Paecilomyces lilacinus*. The microorganism was named as "*Paecilomyces lilacinus* HY-4" and deposited at Gene Bank of Korea Research Institute of Biosciene and Biotehnology on Oct. 27, 1997 (Accession No: KCTC 0395BP).

Example 2

Preservation and Cultivation of the Separated Microorganism *Paecilomyces lilacinus* HY-4

In order to preserve and pre-culture the above separated *Paecilomyces lilacinus* HY-4 for the mass-culture thereof, the present inventors used ME medium represented in Table 2.

TABLE 2

| Ingredient | Amount (%) |
|---|---|
| Malt extract | 2 |
| Glucose | 2 |
| Peptone | 0.1 |

Kept the microorganism in ME plate medium containing 2% agar. Cultured thereof at 26° C. for 15 days until spores were produced, after which added 3 ml of solution in which 0.05% tween 80 and distilled water were mixed to ME agar medium. Then collected spores using a scraper. Suspended the spores in 15% glycerol solution and distributed thereof to each container by 1 ml. Kept the containers at −70° C. refrigerator.

For the culture of the microorganism, autoclaved the ME medium at 121° C. for 20 minutes, inoculated the microorganism thereto and then shaking-cultured at 26° C. with 180 rpm for 4 days.

Example 3

Preparation of Solid Medium and Test of Culture Condition

The present inventors prepared solid medium for mass-production of *Paecilomyces lilacinus* HY-4 separated in the above Example 1 and investigated culture condition. Particularly, after mixing 330 g of wheat bran, 170 g of rice bran and 250 g of water together, put the mixture in a polypropylene bag (50×22×10 cm') for autoclave to which 2 sheets of filter membrane (7×7 cm', effective area diameter 3.5 cm) were attached for air-permeability. After sealing the bag, performed autoclave at 121° C for 30 minutes, resulting in the preparation of the solid medium for mass-production.

Meanwhile, inoculated 0.01-1% of pre-cultured liquid medium onto the above solid medium after the medium was completely cooled. Cultured thereof in a culture room for 3-4 weeks where the temperature was kept at 27° C., the radiation intensity was adjusted to 40 W×2×1.5 and the relative humidity was regulated to 40-70%.

Compared the spores collected from liquid medium cultured in a minimum medium with the spores collected from plate medium. As a result, it was proved that the production of inoculum in liquid medium was superior based on the investigation of culture speed, the generation of contaminated bacteria during culture and the maturing extent of spores after completing the culture. Cultured inoculum at 26° C. for 3 days using CYA medium represented in Table 3 and PDB medium shown in Table 4. Inoculated the above liquid-cultured inoculum solution into solid medium (500 g of dry weight) by 1 ml, 5 ml and 10 ml respectively.

TABLE 3

| | Ingredient | Amount (%) |
|---|---|---|
| Czapek-Dox broth | Bacto saccharose | 3 |
| | Sodium nitrate (NaNO3) | 0.3 |
| | Dipotassium phosphate (K2HPO4) | 0.1 |
| | Mangnessium sulfate (MgSO4) | 0.05 |
| | Potassium chloride (KCl) | 0.001 |
| | Ferrious sulfate (FeSO4) | 0.05 |
| | Yeast extract | 0.5 |

TABLE 4

| | Ingredient | Amount (%) |
|---|---|---|
| PDB (Potato Dextrose Broth) | Potato (Infusion from) | 2 |
| | Bacto Dextrose | 0.2 |
| | Yeast extract | 0.5 |

After smearing the *Paecilomyces lilacinus* HY-4 cultured in the above Example 2 onto CYA and PDA plate medium, cultured thereof at 26° C. or 7-10 days until colonies were formed. After then, took 2-3 colonies from each solid plate medium and put the colonies into 1 ml Erlenmeyer flask containing 200 ml of CAY medium represented in Table 3 or PDB liquid medium represented in Table 4. Shaking-cultured thereof at 26° C. with 180 rpm for 3 days.

After measuring the weight of each solid medium prepared by mixing wheat bran, rice bran and water at the ratio of 4:2:1, put thereof into 125 ml Erlenmeyer flask. Inoculated with the inoculum cultured in liquid medium for 3 days and then cultured thereof at 26° C., with relative humidity (RH) 70% for 6 weeks, during which observed the growth of the inoculum. In order to investigate the growth of bacteria, measured the number of live bacteria (cfu/g) and condria using hemacytometer-counting (spore number/g) method. Took samples from solid medium and measured their weight. Suspended thereof in 20 ml of 0.05% tween 80 solution for successive dilution. Observed by a microscope to count the number of condria. Smeared the diluted solution by 0.1 ml onto plate medium and cultured thereof at 26° C. for 2-4 days, after which investigated all the bacteria. In order to measure the density of microorganism, took samples and counted the number of condria using hemacytometer. Measured specific growth rate by comparing the increased density of condria due to the cell growth with the earlier one, that is, specific growth rate was calculated by subtracting the early condria density from the later condria density after complete growth and then converting the value into log and finally dividing the obtained value by the time obtained by subtracting the early time from the later time.

As a result, the specific growth rate of *Paecilomyces lilacinus* HY-4 cultured in CAY medium was proved to be $0.04\,hr^{-1}$ (inoculated amount was 1 ml), $0.034\,hr^{-1}$ (inoculate amount was 5 ml) and $0.033\,hr^{-1}$ (inoculate amount was 10 ml) on the first week after inoculation, suggesting that specific growth rate was not much affected by the amount of inoculum. Thus, the present inventors confirmed that inoculated amount did not affect the growth of *Paecilomyces lilacinus* HY-4 when CY medium was used as a medium for inoculum (Table 5).

TABLE 5

| Medium | Inoculated amount | Number of conidia (number/g$^{-solid\ medium}$) | | | |
|---|---|---|---|---|---|
| | | 0 | 1$^{st}$ week | 2$^{nd}$ week | 3$^{rd}$ week | 6$^{th}$ week |
| CY | 1 ml | $1.4 \times 10^6$ | $1.5 \times 10^9$ | $6.2 \times 10^9$ | $7.2 \times 10^9$ | $3.9 \times 10^9$ |
| | 5 ml | $6.9 \times 10^6$ | $2.2 \times 10^9$ | $6.9 \times 10^9$ | $4.7 \times 10^9$ | $2.6 \times 10^9$ |
| | 10 ml | $1.4 \times 10^7$ | $3.7 \times 10^9$ | $2.9 \times 10^9$ | $4.2 \times 10^9$ | $3.9 \times 10^9$ |
| PDB | 1 ml | $2.2 \times 10^5$ | $1.3 \times 10^9$ | $5.2 \times 10^9$ | $4.9 \times 10^9$ | $7.2 \times 10^9$ |
| | 5 ml | $1.1 \times 10^6$ | $2.0 \times 10^9$ | $4.3 \times 10^9$ | $5.7 \times 10^9$ | $4.4 \times 10^9$ |
| | 10 ml | $2.2 \times 10^6$ | $1.9 \times 10^9$ | $6.2 \times 10^9$ | $4.6 \times 10^9$ | $3.2 \times 10^9$ |

There was not much difference in using PD medium as a medium for inoculum (0.051, 0.044, 0.040 $hr^{-1}$, respectively). The number of condria was over $10^9$/unit weight of medium and was constantly maintained during 6-week culturing.

Considering all the above results, the present inventors confirmed that more than $10^9$ spores/unit weight of medium could be produced by the solid culture of *Paecilomyces lilacinus* HY-4 on wheat bran medium for 2 weeks.

Example 4

Measurement of the Number of Live Bacteria in Solid Culture

Since the number of live bacteria having insecticidal activity was more important for microbial insecticide, the present inventors measured the density of live bacteria after smearing samples onto CY agar plate medium. Particularly, diluted bacteria with sterilized 0.05% tween 80 solution ($10^{-3}$-$10^{-7}$) and inoculated 100 µl thereof onto antibiotic medium containing antibiotics or general medium. From the next day, counted the number of live bacteria, during which the temperature was maintained at 26° C. Antibiotic medium was prepared by adding oxygall (1.5% /l), a growth inhibitor, to Czapck-Dox agar medium (DIFCO) and additionally adding antibiotics and other growth inhibitors thereto as shown in Table 6.

TABLE 6

| Ingredient | Amount (mg/ml) |
|---|---|
| Ampicilin | 50 |
| Nakidix acid | 10 |
| Rose Bengal | 50 |

Confirmed contamination extent in the general medium and measured the numbers of contaminated bacteria and *Paecilomyces lilacinus* HY-4 in the microorganism test medium containing antibiotics.

As a result, it was confirmed 2-3 days later that *Paecilomyces lilacinus* HY-4 was growing slowly, compared with contaminated bacteria. On the second week after starting the culture, obtained the maximum cell density, which was $10^{12}$ colony forming units (CFU)/unit g of solid medium, that is, massive hyphae were formed, comparing to the result of Example 3 (Table 7).

TABLE 7

| Medium | Inoculated amount | Number of condria (number/g$^{-solid\ medium}$) | | | | |
|---|---|---|---|---|---|---|
| | | 0 | 1$^{st}$ week | 2$^{nd}$ week | 3$^{rd}$ week | 6$^{th}$ week |
| CY | 1 ml | $2.8 \times 10^6$ | $2.0 \times 10^{10}$ | $8.1 \times 10^{12}$ | $1.0 \times 10^{10}$ | $3.9 \times 10^5$ |
| | 5 ml | $1.4 \times 10^7$ | $1.7 \times 10^{10}$ | $4.8 \times 10^{12}$ | $8.7 \times 10^9$ | $8.2 \times 10^5$ |
| | 10 ml | $2.8 \times 10^7$ | $4.4 \times 10^{10}$ | $7.0 \times 10^{12}$ | $6.5 \times 10^9$ | $2.7 \times 10^6$ |
| PDB | 1 ml | $1.3 \times 10^5$ | $1.1 \times 10^{10}$ | $6.0 \times 10^{12}$ | $1.3 \times 10^{11}$ | $1.8 \times 10^6$ |
| | 5 ml | $6.7 \times 10^5$ | $1.4 \times 10^{10}$ | $1.7 \times 10^{12}$ | $4.3 \times 10^{11}$ | $5.5 \times 10^5$ |
| | 10 ml | $1.3 \times 10^6$ | $1.4 \times 10^{10}$ | $6.1 \times 10^{11}$ | $4.4 \times 10^{10}$ | $9.6 \times 10^5$ |

The number of live bacteria was decreased three weeks later and down to the beginning level 6 weeks later. Thus, it was confirmed that the optimum time was on the second week after starting solid culture. Especially two weeks later, most bacteria turned into spores showing high maturity, so that they were expected to have high activity as an insect pathogenic microorganism.

The specific growth rate of the first week was $0.052\,hr^{-1}$ (inoculated amount was 1 ml), $0.043\,hr^{-1}$ (inoculate amount was 5 ml) and $0.042\,hr^{-1}$ (inoculate amount was 10 ml) respectively as *Paecilomyces lilacinus* HY-4 was inoculated in CAY medium for inoculum, and $0.067\,hr^{-1}$ (inoculated amount was 1 ml), $0.059\,hr^{-1}$ (inoculate amount was 5 ml) and $0.055\,hr^{-1}$ (inoculate amount was 10 ml) respectively as

*Paecilomyces lilacinus* HY-4 was inoculated in PD medium for inoculum. Resultingly, such conditions as medium for inoculum and the amount of inoculation could hardly affect on solid culture of *Paecilomyces lilacinus* HY-4, by which basic conditions of solid culture for the mass-culture of *Paecilomyces lilacinus* HY-4 were determined.

Example 5

Investigation of Conditions for Mass-Solid Culture of *Paecilomyces lilacinus* HY-4 by Analysis of Culturing Factors The present inventors investigated the culture conditions for mass-solid culture of *Paecilomyces lilacinus* HY-4. Precisely, prepared basic medium by mixing wheat bran and water at the ratio of 2:1 and regarded each medium condition as a culture factor to search out advantageous factors for yield of mass-solid culture. Used rice bran as a supplementary element for the improvement of ventilation and property of solid medium. Used glucose as an early growth factor, yeast extract as a nitrogen source and a mineral source, cottonseed as a nitrogen source, $KNO_3$ as an inorganic nitrogen source, phosphate as a buffer for pH and used zeolite as an absorbing inorganic additive having sustained releasing property of metallic elements and phosphate. Investigated moisture content as another culture factor. Marked the investigated conditions by t-value and % according to Plackett-Burman method, one of factorial methods. The effect of each variable on bacteria production was determined by calculating the difference between test results done with a variable of higher value and a variable of lower value. Experimental errors were calculated with dummy variables, which were represented by the variation extent presumed in the range of an experimental section. Effective variation (Jeff) and standard deviation (S.E.) of a variable were calculated as Jeff=$(Ed)^2/n$=$(S.E.)^2$. Ed meant each dummy effect and n represented the number of dummy variables. Ex of each variable effect was calculated by Student's t test (t=Ex/S.E.). The basic plan of the test is shown in Table 8.

TABLE 8

| Fermenting factor | Rice bran | Dummy | Zeolite | Moisture | Glucose | Dummy | Yeast extract | Dummy | Contton seed | $KNO_3$ | $K_2HPO_4$ |
|---|---|---|---|---|---|---|---|---|---|---|---|
| Higher value | 2 g | | 1 g | 45.8 | 1% | | 1% | | 1% | 0.5% | 0.1% |
| Lower value | 0 | | 0 | 38.9 | 0 | | 0 | | 0 | 0 | 0 |
| Test group 1 | + | + | − | + | + | + | − | − | − | + | − |
| Test group 2 | + | − | + | + | + | − | − | − | + | − | + |
| Test group 3 | − | + | + | + | − | − | − | + | − | + | + |
| Test group 4 | + | + | + | − | − | − | + | − | + | + | − |
| Test group 5 | + | + | − | − | − | + | − | + | + | − | + |
| Test group 6 | + | − | − | − | + | − | + | + | − | + | + |
| Test group 7 | − | − | − | + | − | + | + | − | + | + | + |
| Test group 8 | − | − | + | − | + | + | − | + | + | + | − |
| Test group 9 | − | + | − | + | + | − | + | + | + | − | − |
| Test group 10 | + | − | + | + | − | + | + | + | − | − | − |
| Test group 11 | − | + | + | − | + | + | + | − | − | − | + |
| Test group 12 | − | − | − | − | − | − | − | − | − | − | − |

How much the each factor had meaning influence on the production of *Paecilomyces lilacinus* HY-4 was summarized in Table 9.

TABLE 9

| | Additives | | Response, t-value/valency(%) | | | |
|---|---|---|---|---|---|---|
| | | | Cell | Medium | Number | |
| Factors | Max-imum | Min-imum | amount (NAcGa) | con-sumption | of live bacteria | Medium pH |
| Rice bran | 2.0 g | 0 | −0.78 | −1.29 | −0.35 | −1.71 (−90%) |
| Zeolite | 1.0 g | 0 | 4.15 (97.5%) | −0.23 | −2.89 (−97.5%) | 5.96 (99.5%) |
| Moisture | 38.9% | 5.8% | 42.47 (99.95%) | 1.52 | 1.12 | 4.90 (99%) |
| Glucose | 1.0% | 0 | −4.70 (−99.5%) | −1.58 | −0.01 | 1.38 |
| Yeast extract | 1.0% | 0 | 0.51 | 0.50 | −0.50 | 0.52 |
| Cotton-seed | 1.0% | 0 | −5.65 (−99%) | −0.78 | 1.27 | 0.52 |
| $KNO_3$ | 0.5% | 0 | −14.63 (−99.95%) | −1.63 | −1.55 | 3.13 (95%) |
| $K_2HPO_4$ | 0.1% | 0 | −6.76 (−99.5%) | −0.29 | −0.51 | −1.86 (−90%) |

The moisture content of a medium was proved to be the most important factor in the event. Precisely, the factor got all "+" in every test fields, suggesting that high moisture content prompted the production of bacteria, accelerated the consuming speed of medium and produced more amount of live bacteria. At that time, the statistical valency was 99.95%

The typical (−) factor was proved to be phosphate. Adding phosphate caused rather interruption in the growth of bacteria. Although rice bran and glucose were confirmed to be (+) factors, starch particles contained in rice bran or glucose was not preferable for *Paecilomyces lilacinus* HY-4 medium. Especially, rice bran accelerated the dryness of medium owing to its too good ventilating property, resulting in the fast drop of moisture content of medium. Thus adding rice bran was beneficial for the maturation of spores but not for the production of bacteria in early stage.

Zeolite was proved to be a culture factor promoting the production of bacteria. Zeolite was observed to moderate the growth inhibition effect caused by phosphate by absorbing and releasing out phosphate. Therefore, zeolite, an absorbent keeping the density of medium low by absorbing culture factors, was proved to be superior to glucose or nitrate that were the factors that bacteria could use easily and fast.

Example 6

Preparation of Microbial Insecticide Containing *Paecilomyces lilacinus* HY-4 for Controlling Soil Pest <6-1> Preparation of Microbial Insecticide Wettable Powders In order to provide the raw powders of *Paecilomyces lilacinus* HY-4 stably, the present inventors prepared wettable powders (WP) that were hydrated when being diluted with water. Particularly, heated the solid medium and then dried thereof. Added surfactants and diluents thereto, and then pulverized thereof. More precisely, dried raw powders in a drier at 70° C. for about 2 hours and then pulverized thereof. Next, mixed the raw powders, surfactants and diluents together well. Pulverized the mixture with a grinder (Jet-O-mill, Aljet) and then tested hydrating capacity for the preparation of microbial insecticide wettable powders (FIG. 1).

In order to confirm the stability of the microbial insecticides for controlling soil pests prepared above, performed preservation test on the wettable powders of the present invention. As a result, the microbial insecticides showed about 38% recovery rate ($2.10 \times 10^7$ CFU/g).

<6-2> Preparation of Microbial Insecticide Granules 1-13

The present inventors prepared granules (GR) that could be used as they were in order to provide *Paecilomyces lilacinus* HY-4 raw-powders stably. Particularly, dried the raw-powders in a dry oven at 70° C. for 2 hours and then pulverized thereof with a grinder (Jet-O-mill, Aljet). Mixed the crushed powders, surfactants, diluents/nutrients and disintegrators together according to the ratios represented in Table 10. Added water (35% of the total weight of the mixture) to the mixture and kneaded thereof. Upon finishing kneading, granulated thereof (diameter: 1 mm, length: 1-5 mm) using Basket type extruder (Fuji powder Co) and then dried in a dry oven at 70° C. Removed dusts by sieving the dried materials with a 16-30 mesh sieve, resulting in the preparation of microbial insecticide granules (FIG. 2).

TABLE 10

| Preparation of granules | Pulverized powders | | Surfactants | | Diluents/Nutrients | | Disintegrators | |
|---|---|---|---|---|---|---|---|---|
| <6-2-1> Preparation 1 | HY-4 spores | 50% | Sodiumtripolyphosphate<br>Polycarboxylate | 15%<br>15% | | | Talc | 20% |
| <6-2-2> Preparation 2 | HY-4 spores | 50% | Polycarboxylate<br>Sodiumlignosulfonate<br>Sodium dialkyl sulfosuccinate | 3%<br>3%<br>1% | Glucose | 10% | Bentonite<br>Calciumcarbonate | 20%<br>13% |
| <6-2-3> Preparation 3 | HY-4 spores | 50% | Sodium alkyl aryl sulfonate<br>Polyoxyethylene alkyl phenyl ether<br>Sodium dialkyl sulfosuccinate | 5%<br>1%<br>1% | Starch | 10% | Talc<br>Dialite | 30%<br>3% |
| <6-2-4> Preparation 4 | HY-4 spores | 50% | Polycarboxylate<br>Polyoxyethylene alkyl phenyl ether<br>Calcium lignosulfonate | 3%<br>1%<br>3% | Starch | 10% | Bentonite<br>Talc | 20%<br>13% |
| <6-2-5> Preparation 5 | HY-4 spores | 50% | Polyoxyethylene alkyl aryl phosphoricester<br>Polyoxyethylene alkyl aryl ether and polyoxyethylene alkyl aryl polymer | 5%<br>3% | Glucose | 10% | Bentonite<br>Talc | 20%<br>12% |
| <6-2-6> Preparation 6 | HY-4 spores | 50% | Polyoxyethylene alkyl phenyl ether<br>Sodiumtripolyphosphate | 1%<br>3% | Starch | 10% | Bentonite<br>Talc | 20%<br>16% |
| <6-2-7> Preparation 7 | HY-4 spores | 50% | Polycarboxylate<br>Polyoxyethylene alkyl aryl ether and polyoxyethylene alkyl aryl polymer | 3%<br>5% | Starch | 10% | Bentonite<br>Kaolin | 20%<br>12% |

TABLE 10-continued

| Preparation of granules | Pulverized powders | | Surfactants | | Diluents/ Nutrients | | Disintegrators | |
|---|---|---|---|---|---|---|---|---|
| <6-2-8> Preparation 8 | HY-4 spores | 50% | Polycarboxylate | 3% | Starch | 10% | Dialite | 20% |
| | | | Sodium alkyl aryl sulfonate | 5% | | | Calciumcarbonate | 11% |
| | | | Sodium dialkyl sulfosuccinate | 1% | | | | |
| <6-2-9> Preparation 9 | HY-4 spores | 50% | Sodiumtripolyphosphate | 3% | Starch | 10% | Bentonite | 10% |
| | | | Polyoxyethylene alkyl aryl phosphoricester | 5% | Dextrin | 10% | Dialite | 12% |
| <6-2-10> Preparation 10 | HY-4 spores | 50% | Polyoxyethylene alkyl aryl polymer special | 5% | Dextrin | 5% | Bentonite | 20% |
| | | | | | | | Talc | 12% |
| | | | Calciumlignosulfonate | 5% | | | | |
| | | | Polycarboxylate | 3% | | | | |
| <6-2-11> Preparation 11 | HY-4 spores | 50% | Polyoxyalkylone alkyl phenylether | 3% | Dextrin | 5% | Calciumcarbonate | 28% |
| | | | | | Starch | 10% | | |
| | | | Sodiumtripolyphosphate | 3% | | | | |
| | | | Sodium dialkyl sulfosuccinate | 1% | | | | |
| <6-2-12> Preparation 12 | HY-4 spores | 50% | Sodium lignosulfonate | 3% | Glucose | 10% | Kaolin | 20% |
| | | | | | | | Talc | 14% |
| | | | Polyoxyethylene alkyl aryl ether polymer | 3% | | | | |
| <6-2-13> Preparation 13 | HY-4 spores | 50% | Polyoxyethylene nonyl phenyl ether | 3% | Dextrin | 5% | Kaolin | 20% |
| | | | | | | | Dialite | 19% |
| | | | Sodium sulfonate naphthalene formaldehyde | 2% | | | | |
| | | | Sodium dialkyl sulfosuccinate | 1% | | | | |

In order to confirm the stability of the microbial insecticides for controlling soil pests prepared above, performed preservation test on the granules of the present invention. As a result, the microbial insecticides showed about 52% recovery rate ($3.40 \times 10^7$ CFU/g).

<6-3> Preparation of Formulations for Capsulation of Microbial Insecticide

The present inventors prepared formulations for capsulation of microbial insecticide having the same effect as the microbial insecticide granules for controlling soil pests prepared in the above Example 6. Particularly, mixed 11% soybean flour, 6% mung beans, 4% rice flour, 4% potato starch, 4% rye flour and 3% yellow earth together and autoclaved thereof at 121° C. for 20 minutes. Before completely cooling down, mixed thereof well again and then cool it down in cold water. Mixed thoroughly over 1 minute using a stirrer (d=5 cm, over 200 rpm). While keeping on stirring, added additives and *Paecilomyces lilacinus* HY-4 (Accession No: KCTC 0395BP) spores and mixed well again, resulting in the preparation of formulations for capsulation of microbial insecticide for controlling soil pests.

Example 7

Security of Test Insect

The present inventors secured test insects to confirm the insecticidal effect of *Paecilomyces lilacinus* HY-4 on soil pests. Particularly used *Adoretus tenuinaculatus* among gold bugs that caused trouble in golf courses and parks, a kind of soil pests, as a test insect. The imagoes (adult insects) were collected in Yusung country club, Taejeon, Korea and bred through generations using a chestnut tree as a host plant. Tests were done within 2-4 generations. The larvae were bred with artificial feeds (sawdust:bed soil:water=5:3:2). Both imagoes and larvae of the test insects were bred in cages (30 cm×30 cm×50 cm) in which temperature was maintained at 25±2° C., and relative humidity was kept 60-70%.

Example 8

Confirmation of the Insecticidal Effect by the Dipping Method

The present inventors confirmed the insecticidal effect of *Paecilomyces lilacinus* HY-4 of the present invention on gold bugs by dipping method. Particularly, shaking cultured *Paecilomyces lilacinus* HY-4 on ME medium for 3 days (26° C., 180 rpm). Measured the density of spores with hemacytometer and adjusted the density to $1 \times 10^8$ spores/ml using distilled water containing 0.05% tween-80. After dipping 10 larvae each from $1^{st}$ instar, $2^{nd}$ instar and $3^{rd}$ instar of *Adoretus tenuinaculatus* in spore suspension for 10 seconds, transferred them to artificial feeds (sawdust:bed soil:water=5:3:2) and raised them at 26-28° C. in dark condition. While keeping required humidity for 15 days, investigated pathogenesis. At that time, regarded insects on which hyphae of fungus were generated as dead insects and insects grown to next instar as live insects. Counted both numbers and presented them with percentage. All experiments were performed 5 times. Used distilled water containing 0.05% tween-80 for a control group.

Figure 3:
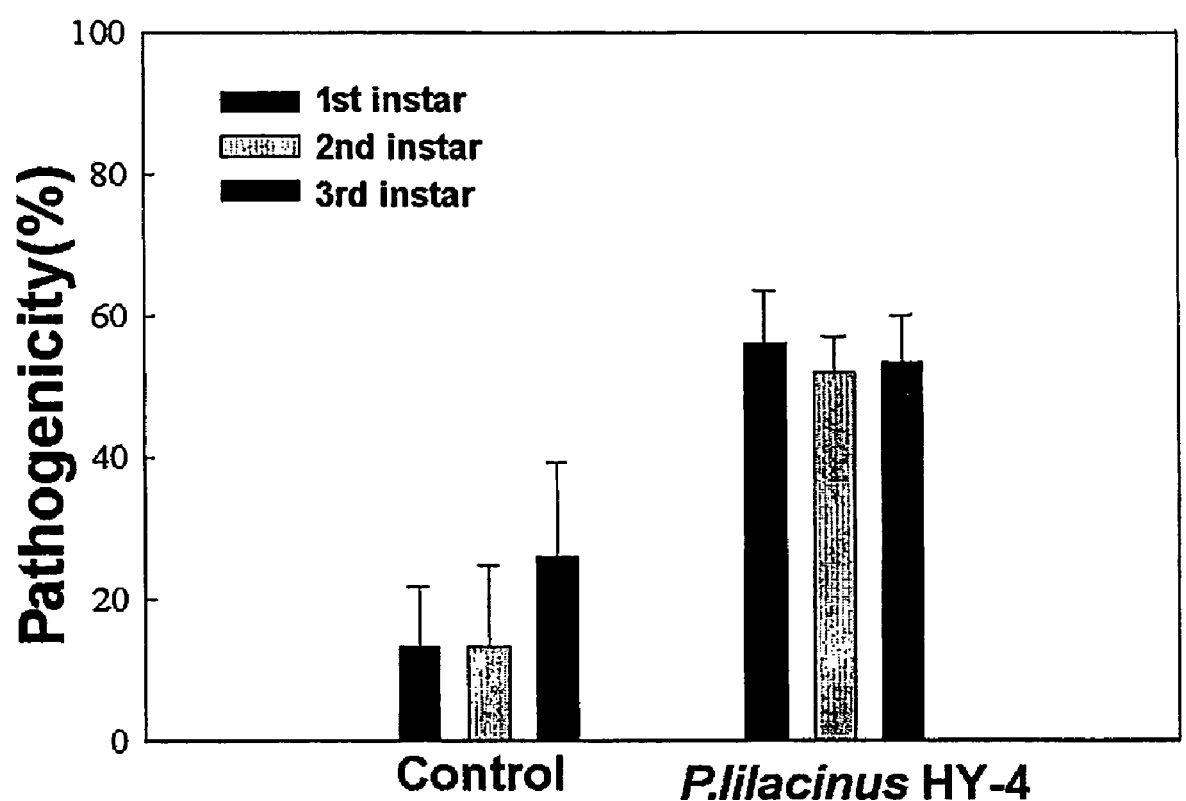
FIG. 3 is a graph showing the insecticidal effect of the *Paecilomyces lilacinus* HY-4 of the present invention measured by dipping method.
Figure 4:
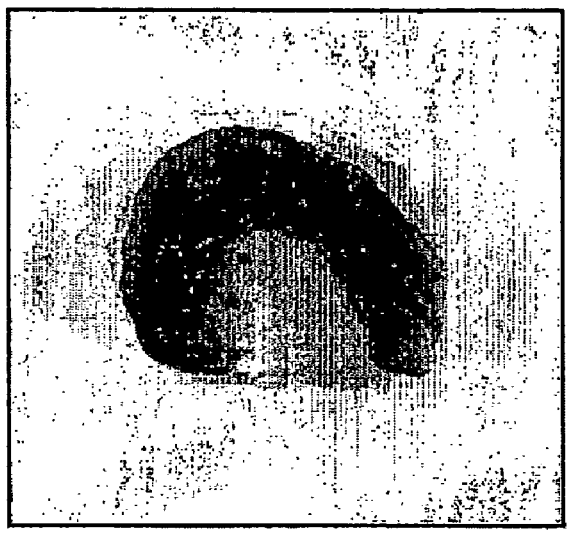
FIG. 4 is a set of photographs showing the larva of an *Adoretus tenuimaculatus* killed by the infection with the *Paecilomyces lilacinus* HY-4 of the present invention.
Figure 4:
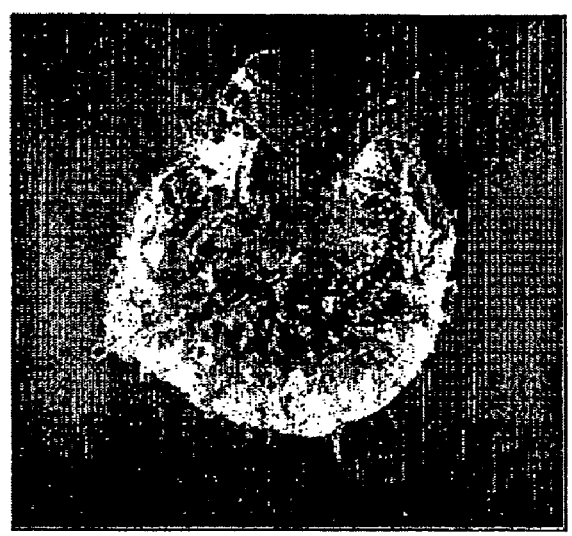

As a result, *Paecilomyces lilacinus* HY-4 of the present invention showed excellent insecticidal effect (52-56%) while control group showed just 13-26% insecticidal effect (FIG. 3). In addition, more larvae of *Adoretus tenuinaculatus* were confirmed to be infected with *Paecilomyces lilacinus* HY-4 as time went (FIG. 4).

Example 9

Confirmation of Insecticidal Effect by the Contact Toxicity Test

The present inventors confirmed the insecticidal effect of *Paecilomyces lilacinus* HY-4 of the present invention on gold bugs by contact toxicity test. Particularly, shaking cultured *Paecilomyces lilacinus* HY-4 on ME medium for 3 days (26° C., 180 rpm). Put 750 g of solid medium (wheat bran:rice bran:water=4:2:3) into a polypropylen bag (50×22×10 cm') having 2 sheets of filter membranes (7×7 cm', effective area diameter 3.5 cm) in it for air permeability and then sealed, which was autoclaved at 121° C. for 30 minutes. Inoculated 9-10 ml of the culture fluid on the solid medium prepared above and then cultured thereof in a culture room for 3-4 weeks in which temperature was maintained at 27° C., the radiation intensity was kept 40 W×2×1.5 and the relative humidity was kept 40-70%. Measured the density of spores with hemacytometer. After crushing the solid medium, adjusted the density to $1 \times 10^8$ spores/ml and then distributed thereof over humidified artificial feeds (sawdust:bed soil: water=5:3:2). Transferred 10 larvae each from $1^{st}$ instar, $2^{nd}$ instar and $3^{rd}$ instar of *Adoretus tenuinaculatus* into the above artificial feeds and raised them at 26-28° C. in dark condition. While keeping required humidity for 15 days, investigated pathogenesis. At that time, regarded insects on which hyphae of fungus were generated as dead insects and insects grown to next instar as live insects. Counted those numbers and presented them with percentage. All experiments were performed 5 times. Used distilled water containing 0.05% tween-80 for a control group.

Figure 5:
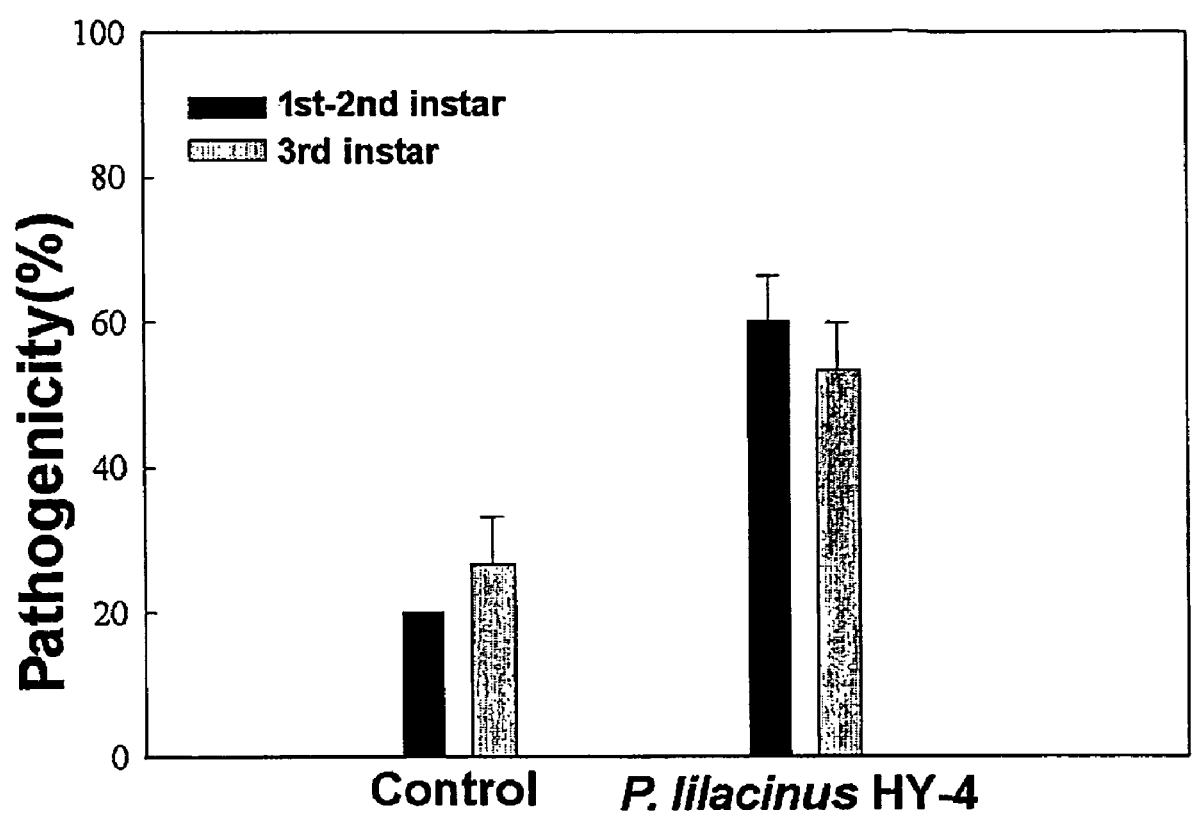
FIG. 5 is a graph showing the insecticidal effect of the *Paecilomyces lilacinus* HY-4 of the present invention measured by contact toxicity test.

As a result, *Paecilomyces lilacinus* HY-4 of the present invention showed excellent insecticidal effect (53-60%) while control group showed just 20-27% insecticidal effect (FIG. 5).

INDUSTRIAL APPLICABILITY

As described hereinbefore, the microbial insecticide containing a *Paecilomyces* genus microorganism of the present invention having insecticidal activity to soil pests was proved to have excellent insecticidal effect on soil pests including the larvae of gold bugs, a kind of soil pests harming agricultural products. Therefore, it can be effectively used as an environment-compatible insecticide to prevent the soil pests from farmland crops.

What is claimed is:

1. An isolated *Paecilomyces lilacinus* HY-4 fungus having insecticidal activity to soil pests, deposited at Gene Bank of Korea Research Institute of Bioscience and Biotechnology under Accession No: KCTC 0395BP.

2. A microbial insecticide for controlling soil pests containing the isolated *Paecilomyces lilacinus* HY-4 fungus of claim 1.

3. The microbial insecticide of claim 2, wherein the microbial insecticide is prepared in the form of wettable powders, granules or capsules.

4. The microbial insecticide of claim 3, wherein the wettable powders are prepared by:
   pulverizing dry solid media inoculated with a *Paecilomyces lilacinus* fungus designated HY-4 deposited at Gene Bank of Korea Research Institute of Bioscience and Biotechnology under Accession No: KCTC 0395BP, thereby generating a pulverized powder; and
   adding surfactants and diluents/nutrients to the pulverized powder.

5. The microbial insecticide of claim 3, wherein the granules are prepared by pulverizing dry solid media inoculated with a *Paecilomyces lilacinus* fungus designated HY-4 deposited at Gene Bank of Korea Research Institute of Bioscience and Biotechnology under Accession No: KCTC 0395BP, thereby generating a pulverized powder; and
   adding surfactants, diluents/nutrients and disintegrators to the pulverized powder.

6. The insecticide as set forth in claim 5, wherein the granules comprise by weight, 30-83 parts pulverized powders of the microorganism spores, 2-30 parts surfactants, 5-20 parts diluents and 10-40 parts disintegrators.

7. The insecticide as set forth in claim 6, wherein the granules additionally contain one or more components selected from a group consisting of surface active agents, inactive carriers, preservatives, wetting agents, attractants, encapsulating agents, binders, emulsifiers, dyes, UV protectors, buffers and fluids.

8. The microbial insecticide of claim 4, wherein the insecticide contains one or more surfactants selected from a group consisting of polycarboxylate, sodium lignosulfonate, calcium lignosulfonate, sodium dialkyl sulfosuccinate, sodium alkyl sulfonate, polyoxyethylene alkyl phenyl ether, sodium tripolyphosphate, sodium alkyl aryl sulfonate, polyoxyethylene alkyl phenyl ether, polyoxyethylene alkyl aryl phosphoric ester, polyoxyethylene alkyl aryl ether, polyoxyethylene alkyl aryl polymer, polyoxyethylene alkyl aryl polymer special, polyoxyalkylene alkyl phenyl ether, polyoxyethylene nonyl phenyl ether, sodium sulfonate naphthalene formaldehyde, triton 100 and tween 80.

9. The microbial insecticide of claim 4, wherein the insecticide contains one or more diluents/nutrients selected from a group consisting of soybean flour, rice, wheat, yellow earth, diatomaceous earth, dextrin, glucose and starch.

10. The insecticide as set forth in claim 5, wherein the insecticide contains one or more disintegrators selected from a group consisting of bentonite, talc, dialite, kaolin and calcium carbonate.

11. The microbial insecticide of claim 5, wherein the insecticide contains one or more surfactants selected from a group consisting of polycarboxylate, sodium lignosulfonate, calcium lignosulfonate, sodium dialkyl sulfosuccinate, sodium alkyl sulfonate, polyoxyethylene alkyl phenyl ether, sodium tripolyphosphate, sodium alkyl aryl sulfonate, polyoxyethylene alkyl phenyl ether, polyoxyethylene alkyl aryl phosphoric ester, polyoxyethylene alkyl aryl ether, polyoxyethylene alkyl aryl polymer, polyoxyethylene alkyl aryl polymer special, polyoxyalkylene alkyl phenyl ether, polyoxyethylene nonyl phenyl ether, sodium sulfonate naphthalene formaldehyde, triton 100 and tween 80.

12. The microbial insecticide of claim 6, wherein the insecticide contains one or more surfactants selected from a group consisting of polycarboxylate, sodium lignosulfonate, calcium lignosulfonate, sodium dialkyl sulfosuccinate, sodium alkyl sulfonate, polyoxyethylene alkyl phenyl ether, sodium tripolyphosphate, sodium alkyl aryl sulfonate, polyoxyethylene alkyl phenyl ether, polyoxyethylene alkyl aryl phosphoric ester, polyoxyethylene alkyl aryl ether, polyoxyethylene alkyl aryl polymer, polyoxyethylene alkyl aryl polymer special, polyoxyalkylene alkyl phenyl ether, polyoxyethylene nonyl phenyl ether, sodium sulfonate naphthalene formaldehyde, triton 100 and tween 80.

13. The insecticide of claim 5, wherein the insecticide contains one or more diluents/nutrients selected from a group consisting of soybean flour, rice, wheat, yellow earth, diatomaceous earth, dextrin, glucose and starch.

* * * * *